United States Patent [19]

Hörpel et al.

[11] Patent Number: 5,359,003
[45] Date of Patent: Oct. 25, 1994

[54] POLYSULFIDE DERIVATIVES

[75] Inventors: Gerhard Hörpel, Nottuln; Karl-Heinz Nordsiek, Marl, both of Fed. Rep. of Germany

[73] Assignee: Huls Aktiengesellschaft, Marl, Fed. Rep. of Germany

[21] Appl. No.: 104,681

[22] Filed: Aug. 11, 1993

Related U.S. Application Data

[62] Division of Ser. No. 624,009, Dec. 7, 1990, Pat. No. 5,241,108.

[30] Foreign Application Priority Data

Dec. 12, 1989 [DE] Fed. Rep. of Germany ........ 3941002

[51] Int. Cl.$^5$ ................................................ C08F 8/00
[52] U.S. Cl. .................................... 525/167; 525/55; 525/57; 525/88; 525/95; 525/98; 525/165; 525/328.2; 525/328.3; 525/329.5; 525/331.8; 525/331.9; 525/332.6; 525/333.1; 525/333.5; 525/343; 524/81; 558/230; 558/243; 558/261
[58] Field of Search .......... 529/55, 57, 88, 95, 529/98, 165, 167, 328.2, 328.3, 329.5, 331.8, 331.9, 332.6, 333.1, 333.2, 333.5, 343; 558/230, 243, 261; 524/81

[56] References Cited

U.S. PATENT DOCUMENTS

| | | | |
|---|---|---|---|
| 3,778,370 | 12/1973 | Kennedy et al. | 252/42.7 |
| 3,867,543 | 2/1975 | Kohn | 424/301 |
| 3,988,471 | 10/1976 | Kohn | 424/301 |
| 4,338,207 | 7/1982 | Adams | 252/47.5 |
| 4,456,509 | 6/1984 | Habeeb et al. | 204/59 |
| 4,566,982 | 1/1986 | Habeeb et al. | 252/33.6 |
| 4,786,746 | 11/1988 | Miljkovic | 560/302 |
| 4,965,326 | 10/1990 | Horpel et al. | 526/84 |

FOREIGN PATENT DOCUMENTS 0519998  4/1940  United Kingdom .

Primary Examiner—Samuel A. Acquah
Attorney, Agent, or Firm—Millen, White, Zelano & Branigan

[57] ABSTRACT

Polysulfide derivatives, having the general formula (A—S—S—)$_2$ X—S—S—A processes for their production and their use for crosslinking of reversion-stable rubber vulcanizates are provided. Crosslinking with reduced reversion and loss of elastomeric properties with age is achieved by the crosslinking system provided by the invention.

4 Claims, No Drawings

POLYSULFIDE DERIVATIVES

This is a division of application Ser. No. 07/624,009 filed Dec. 7, 1990, now U.S. Pat. No. 5,241,108.

CROSS-REFERENCE TO RELATED APPLICATION

This application is related to concurrently filed copending application Ser. No. 07/624,176, entitled "Aromatic Dithiocarboxylic Acid Vulcanization Accelerators and Method of Their Use" by Horpël et al., based on German Application P 39 41 001.3, filed Dec. 12, 1989.

BACKGROUND OF THE INVENTION

The invention relates to new sulfide derivatives of aromatic dithiocarboxylic acids, a process for their production and their use as nitrosamine-free crosslinking agents in rubbers for improvements in reversion stability. The polysulfide derivatives according to the invention have the general formula $$(A-S-S-)_zX-S-S-A'$$

Crosslinking rubber with sulfur, or sulfur donors and accelerator systems, generally yields vulcanizates, whose polymer chains in the beginning phase are linked by polysulfide sulfur crosslinking. Polysulfide-linked vulcanizates with a great number of crosslinks lead to optimal results (cf. A. V. Chapman, M. Porter "Sulfur Vulcanization Chemistry" in "Natural Rubber Science and Technology," A. D. Roberts, ed Oxford Press 1988). This applies to mechanical strength and especially to tear propagation resistance and also to abrasion resistance. But there is a disadvantage in such sulfur-containing systems insofar as they are subject to reversion which encompasses the decline of the vulcanizate properties during the vulcanization process and the anaerobic aging of the resultant vulcanized products during dynamic stress. The theories on the mechanism are that under thermal stress a breakdown of the polysulfide bridges to the monosulfide arrangement occurs. The sulfur thus being released is added to polymer segments and thus increases their glass transition temperature (Tg) but also catalyzes the attack of the oxygen on the vulcanizate. Both effects lead to damage of the crosslinks. These secondary reactions of the sulfur, which already begin during the vulcanization process as a function of the reaction time and reaction temperature, substantially affect the performance limits of the elastomers and therefore require limitation in view of the optimal configuration of the production process (see in this connection also A. V. Chapman, M. Porter in the above-cited article).

The use of the so-called EV systems represents an attempt to reduce the secondary reactions of the sulfur; they are system which consist of increased amounts of vulcanization accelerators with simultaneously minimal amounts of sulfur. But as a result of the faster prevulcanization, the processing reliability is adversely changed. There is added to this—and this is even more important—the preprogrammed impairing of the abrasion resistance, the tear propagation resistance and the cord adhesion, as is consistent with known tire technology (cf. P. M. Lewis "Vulcanisate structure and it effects on properties" in NR-Technologie, Quarterly Volume 17, Part 4, page 57ff., 1986).

To provide thermally stable vulcanizates, polysulfide derivatives were proposed (cf. DE-AS 22 65 382), which with the addition of thermal energy, release polysulfide segments. These polysulfide derivatives contain conventional accelerator systems, e.g., dithiocarbamoyl structures, as initial groups (A). But a considerable disadvantage of the dithiocarbamate system is that during the vulcanization process, nitrosamines are formed, which result by the nitrosation of the decomposition products (amines) of the dithiocarbamates unstable under these conditions. According to today's knowledge, nitrosamines are considered a health hazard, since they form mostly carcinogenic metabolites (cf. Umschau 1985 (1), 24). Amine-free polysulfide derivatives as crosslinking agents are also known, but they exhibit a completely unsatisfactory level of performance.

SUMMARY OF THE INVENTION

The principal object of this invention, therefore, is to provide thermally stable vulcanizates while avoiding the formation of nitrosamines.

To attain the objects of this invention, this invention provides a sulfide derivative of an aromatic dithiocarboxylic acid of the formula $$(A-S-S-)_zX-S-S-A',$$

wherein

A and A' are, independently, amine-free aromatic thiocarbonyl groups of formula I

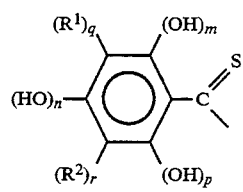

wherein n, m, p, q and r are 0 or 1 and the sum of n+m+p is at least 1, $R^1$ and $R^2$ are, independently, $C_1$-$C_{10}$-alkyl radicals, alkenyl radicals with up to 10 carbon atoms ($C_1$-$C_{10}$) or aralkyl radicals with up to 15 carbon atoms, z is a natural number with $0<z<50$, and is a divalent (z=1) or polyvalent (z>1) linear or branched aliphatic, cycloaliphatic or araliphatic compound, or polymer, preferably an ethylenically unsaturated hydrocarbon polymer, having a degree of polymerization up to 50 and a valence of at least two, and where z=1, X is a $C_1$-$C_{30}$-alkylene radical, or an alkenylene radical with up to 30 carbon atoms ($C_1$-$C_{30}$), or aralkylene radical with up to 40 carbon atoms and where $1<z\leq 4$, X is a polyvalent $C_1$-$C_{20z}$ alkane radical or a polyvalent alkene radical with up to 20z carbon atoms or a polyvalent arylalkane radical with up to 20z carbon atoms.

Also provided are methods for the production of said sulfide derivatives of an aromatic dithiocarboxylic acid, wherein a dithiocarboxylic acid of the formula

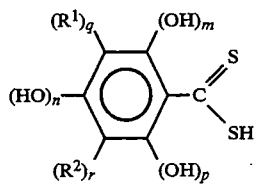

in which n, m, p, q and r are 0 or 1 and the sum of n+m+q is at least 1, $R^1$ and $R^2$ are, independently, $C_1$–$C_{10}$-alkyl radicals, alkenyl radicals with up to 10 carbon atoms ($C_1$–$C_{10}$), or aralkyl radicals with up to 15 C atoms, is reacted at a temperature between −10° C. to +60° C. and pH between 6 and 9 with the Bunte salt of a divalent or polyvalent alkyl compound, of the formula

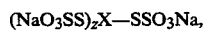

(NaO$_3$SS)$_z$X—SSO$_3$Na, in which
z represents a natural number between 0 and 50, and
X is a divalent (z=1) or polyvalent (z greater than 1) linear or branched aliphatic, cycloaliphatic or araliphatic compound or polymer having a degree of polymerization of up to 50 and a valence of at least two,
  for z=1, X is: an alkylene radical with 1 to 30 carbon atoms, an alkenylene radical with up to 30 carbon atoms ($C_1$–$C_{30}$), or
  an aralkylene radical with up to 40 carbon atoms for $1<z\leq 4$, X is a polyvalent $C_1$–$C_{20z}$-alkane, polyvalent alkene with up to 20z carbon atoms ($C_1$–$C_{20z}$), or
  polyvalent arylalkane with up to 20z carbon atoms.

In another aspect, this invention provides a process for vulcanizing rubber which comprises blending a compound of Formula I and a primary accelerator with an organic polymeric rubber to form a mixture and heating the mixture to a temperature in the range of 100° C. to 250° C.

Furthermore, crosslinked rubbers produced by this vulcanization process are provided.

An underlying inventive concept of the principal object of the invention is manifested by employing instead of oligomer S bridges for crosslinks, stable carbon-containing bridges (X) with amine-free phenol thiocarbonyl initial groups are combined according to the above described formula:

(A—S—S—)$_z$X—S—S—A′.

Preferred initial groups A and A′ are 4-hydroxy-3,5-dialkyl-benzene-thiocarbonyl groups, and optionally instead of the phenol group a phenolate group is also advantageous. Especially preferred is the 4-hydroxy-3,5-di-tert-butyl-benzene-thiocarbonyl initial group or the corresponding phenolate. These can be obtained from the aromatic dithiocarboxylic acids described above and produced in accordance with the procedures set forth in the examples or the procedures referred to in copending application Ser. No. 07/624,176, filed concurrently herewith.

For crosslinking bridges X, the large number of possible compounds is limited by the availability of initial compounds of dichlorides and dithioles. Preferred crosslinking bridges X are divalent linear alkylene groups, and especially preferably, z=1, X is ethylene and $R^1$ and $R^2$ are lower alkyl.

Other crosslinking bridges include

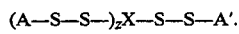

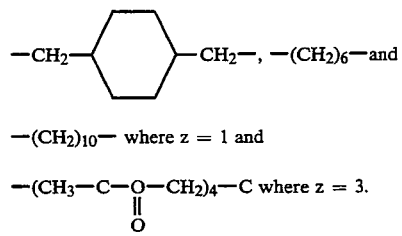

—(CH$_2$)$_{10}$— where z = 1 and

—(CH$_3$—C—O—CH$_2$)$_4$—C where z = 3.
      ||
      O

Examples of substituents for $R^1$ and $R^2$ include

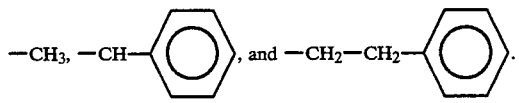

Natural and synthetic rubbers are suitable as rubbers for the crosslinking process according to the invention. Preferred synthetic rubbers are, e.g., styrene-butadiene copolymers, polybutadienes, polyisoprenes, integral rubbers (as described in DE-OS 37 10 002, 37 24 871, 38 04 574) or their blends, but also nitrile, chloroprene, butyl, EPDM rubbers and others.

There are no limitations in regard to other usual rubber additives such as, e.g., fillers, plasticizers, tackifiers, accelerators, activators, stearic acid, waxes, aging and ozone protective agents, expanding agents, dyes as well as pigments. The production of a vulcanizing system with the above-mentioned rubber additives takes place according to the usual processes known to one skilled in the art.

The vulcanization is performed at temperatures between 100° and 250° C., preferably between 120° and 240° C. The vulcanization also occurs according to usual processes known to one skilled in the art.

The polysulfide derivatives according to the invention exhibit advantages in the formulations to be used relative to reversion stability after prolonged vulcanization time and vulcanization temperatures. At the same time they exhibit a considerably smaller decline in performance from elastomer aging and are safe in regard to danger of generating carcinogenic nitrosamines.

They combine in themselves a double function of crosslinking reagent (bis-thio-alkane bridges) and antioxidant (sterically hindered phenol), and the latter exhibits the additional advantage of being fixed in the network.

The process for the production of the above-mentioned polysulfide derivatives by reaction of a dithiocarboxylic acid of the formula

A—SH, where A has the above-mentioned meaning, with the Bunte salt of the divalent or polyvalent alkyl compound of formula

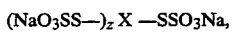

(NaO$_3$SS—)$_z$ X —SSO$_3$Na, where and X and z also have the above-mentioned meanings, is preferably conducted so that 2 moles of the dithiocarboxylic acid as a solution in a water-miscible organic solvent is added to 1 mole of the Bunte salt as an aqueous or organic water-miscible solution at temperatures of −10° to +60° C., preferably 20° to 40° C., and the pH of the reaction solution and all educts are kept constant between 6 and 9, preferably between 7 and 8.

The preferred organic solvent is tetrahydrofuran (THF).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, if any, cited above and below, and of corresponding application Federal Republic of Germany P 39 41 002.1, filed Dec. 12, 1989, are hereby incorporated by reference.

Production examples

1. Bunte salt of 1,2-dichloroethane 40.16 g of 1,2-dichloroethane (97.5%) is refluxed with 198.40 g of sodium thiosulfate pentahydrate in a mixture of 800 ml of water and 650 ml of ethanol for 15 hours. The resulting bis-Bunte salt is used without further work up for the next stages.

2. DBCA: 4-Hydroxy-3,5-di-tert-butyl-benzenedithiocarboxylic acid or DBCAK: the corresponding potassium salt 1031.7 g of di-tert-butyl phenol under nitrogen is dissolved in 2.5 liters of THF in a nitrogen-flushed 6-liter three-neck flask with reflux condenser, dropping funnel and stirrer. After introduction of 561.0 g of KOH powder (exothermic reaction), the flask contents are cooled to 10° C. At this temperature, 380.5 g of carbon disulfide is added over 5 hours and then allowed to post-react for 15 hours at that temperature. The resulting solid is suctioned off, rewashed with cold acetone and dried at room temperature in a vacuum drying cabinet. 1,525 g of the crude product of DBCAK was present (85% yield).

3. DBEB: 1,2-Bis-(4-hydroxy—3,5-di-tert-butyl-benzenethio-carbonyldithio)ethane (More proper name according to IUPAC: bis-[4-hydroxy-3,5-di-tert-butyl-benzene-dithiocarboxylic acid (dithioperoxo)]1,2-ethanediyl ester)

294.1 g of DBCAK (from 2.) as 10% aqueous solution is mixed with 1,200 ml of THF and adjusted to pH 7 with acetic acid. Into this receiver there are added, on the one hand, 1,516.8 g of Bunte salt solution from 1. (corresponds to 0.4 mole of Bunte salt) and parallel with it, 67.3 g of a 37% formaldehyde solution over a period of 3 hours. Then the pH is adjusted to 8 and allowed to post-react for 15 hours at room temperature as well as 5 hours at 40° C. 171 g of crude product can be isolated, which can be recrystallized from petroleum ether.

| Elementary analysis: | C | H | O | S |
|---|---|---|---|---|
| Cld: | 58.67 | 7.08 | 4.88 | 29.36 |
| Fnd: | 58.37 | 7.15 | | 27 |

Characteristic IR bands (in cm$^{-1}$): 3 600, 2 960, 1 580, 1 215

$^{13}$C NMR spectrum (in CDCl$_{13}$): Peaks at 30.015, 34.277, 36.611 , 76.570, 76.922, 125.295, 135.564, 136.036, 159.086, 225.316 ppm.

Vulcanization examples

Experimental

All the tread vulcanizates described below were produced as follows:

With an Internal Mixer, model GK 2 of the company Werner and Pfleiderer, at a rotor speed of 50 rpm and a jacket temperature of 40° C., the following base mixture is prepared:

| | |
|---|---|
| rubber | 100 |
| ZnO | 3 phr |
| | (lbs. per hundred rubber) |
| stearic acid | 2 phr |
| aromatic plasticizer oil | 10 phr |
| Black N-339 | 50 phr |
| crosslinking agent | see tables |

The modulus at 100 or 300% elongation was determined according to DIN 53 504.

The tear resistance was determined according to Pohle (cf. S. Bostroem, Kautschuk-Handbuch [Rubber Manual], Volume 5, page 123).

The permanent set was determined according to DIN 53 518.

The hardness (Shore A) was determined according to DIN 53 505.

The rebound (elasticity) was determined according to DIN 53 512.

The abrasion was determined according to DIN 53 516.

The compression set was determined according to DIN 53 517.

The heat buildup test takes place according to DIN 53 533, part 3, with the Goodrich Flexometer, identified in the test part as method 1. Moreover, the following more onerous conditions were selected, which are identified in the test part as method 5:

Load: 500 N, starting temperature: 50° C., time: 25 minutes.

Ball fatigue test at the respective stresses was determined according to S. Bastroem, Kautschuk-Handbuch, 5th volume, Berliner Union, Stuttgart, pp. 149, 150.

The vulcametry was performed according to DIN 53 529.

TABLE I

Example 1
Vulcanization of a premasticated NR (Mooney 70; RRS No. 3) with DBEB (7.0 phr) at elevated reaction temperature (1st part).

| | Example Vulcanization temperature | | | | | |
|---|---|---|---|---|---|---|
| | 150° C. | 180° C. | | | | |
| | Vulcanization time in min. | | | | | |
| | 30 | 5 | 10 | 15 | 20 | 30 |
| Vulcameter 150° C. | | | | | | |
| t$_{10}$ min | 5.7 | | | | | |
| t$_{90}$ min | 12.1 | | | | | |
| Delta t min | 6.4 | | | | | |
| Tensile strength MPa | 21.6 | 20.8 | 19.1 | 18.9 | 18.0 | 17.2 |
| Elongation at break % | 581 | 528 | 498 | 476 | 468 | 445 |
| Modulus | | | | | | |
| 100% MPa | 1.4 | 1.5 | 1.6 | 1.6 | 1.6 | 1.5 |
| 300% MPa | 8.3 | 8.8 | 9.1 | 9.2 | 9.3 | 9.1 |

TABLE I-continued

Example 1
Vulcanization of a premasticated NR (Mooney 70; RRS No. 3) with DBEB (7.0 phr) at elevated reaction temperature (1st part).

| Example Vulcanization temperature | 150° C. | 180° C. | | | |
|---|---|---|---|---|---|
| | | Vulcanization time in min. | | | |
| | 30 | 5 | 10 | 15 | 20 | 30 |

| | 30 | 5 | 10 | 15 | 20 | 30 |
|---|---|---|---|---|---|---|
| Tear resistance N/mm | 81 | 84 | 78 | 72 | 72 | 69 |
| Permanent set % | 10 | 10 | 10 | 11 | 10 | 11 |
| Hardness | | | | | | |
| 22° C. Sh.A | 62 | 62 | 61 | 62 | 62 | 61 |
| 75° C. Sh.A | 58 | 54 | 54 | 53 | 54 | 53 |
| Elasticity | | | | | | |
| 22° C. % | 47 | 46 | 47 | 47 | 47 | 46 |
| 75° C. % | 58 | 57 | 56 | 56 | 56 | 56 |
| DIN abrasion mm$^3$ | 133 | 125 | 123 | 131 | 135 | 134 |
| specific weight g/mm$^3$ | 1.10 | 1.10 | 1.10 | 1.10 | 1.10 | 1.10 |

TABLE II

Comparison example 1
Vulcanization of a premasticated NR (Mooney 70; RRS No. 3) with the vulcanization system sulfur/CBS (2.5/0.6 phr) at elevated reaction temperature

| Example Vulcanization temperature | 150° C. | 180° C. | | | |
|---|---|---|---|---|---|
| | | Vulcanization time in min. | | | |

| | 30 | 5 | 10 | 15 | 20 | 30 |
|---|---|---|---|---|---|---|
| Vulcameter 150° C. | | | | | | |
| t$_{10}$ min | 7.6 | | | | | |
| t$_{90}$ min | 12.5 | | | | | |
| Delta t min | 4.9 | | | | | |
| Tensile strength MPa | 23.3 | 18.8 | 17.5 | 14.5 | 13.8 | 11.9 |
| Elongation at break % | 558 | 498 | 424 | 510 | 526 | 483 |
| Modulus | | | | | | |
| 100% MPa | 2.0 | 1.6 | 1.3 | 1.3 | 1.1 | 1.1 |
| 300% MPa | 10.1 | 8.5 | 6.6 | 5.7 | 5.4 | 5.3 |
| Tear resistance N/mm | 74 | 64 | 26 | 19 | 18 | 16 |
| Permanent set % | 16 | 15 | 13 | 9 | 11 | 10 |
| Hardness | | | | | | |
| 22° C. Sh.A | 61 | 58 | 55 | 54 | 53 | 52 |
| 75° C. Sh.A | 57 | 52 | 46 | 45 | 44 | 43 |
| Elasticity | | | | | | |
| 22° C. % | 48 | 50 | 47 | 45 | 46 | 44 |
| 75° C. % | 60 | 60 | 54 | 51 | 50 | 49 |
| DIN abrasion mm$^3$ | 129 | 121 | 148 | 189 | 224 | 247 |
| specific weight g/mm$^3$ | 1.10 | 1.10 | 1.10 | 1.10 | 1.10 | 1.10 |

TABLE III

Example 2
Vulcanization of an SBR 1 500 with DBEB
7 phr DBEB

| Vulcanization system Properties | Vulcanization at 150° C. in 40 Min. | after 7 days aging at | | | |
|---|---|---|---|---|---|
| | | 100° C. | 110° C. | 120° C. | 130° C. |
| Tensile strength MPa | 20.9 | 16.2 | 15.9 | 13.2 | 5.8 |
| Elongation at break % | 478 | 278 | 247 | 181 | 58 |
| Modulus | | | | | |
| 100% MPa | 2.2 | 3.6 | 4.1 | 5.1 | — |
| 300% MPa | 10.6 | — | — | — | — |
| Tear resistance N/mm | 28 | 26 | 16 | 9 | — |
| Permanent set % | 9 | 4 | 3 | 2 | 1 |
| Hardness | | | | | |
| 22° C. Sh.A | 64 | 68 | 71 | 73 | 76 |
| 75° C. Sh.A | 60 | 63 | 68 | 69 | 73 |
| Elasticity | | | | | |
| 22° C. % | 45 | 52 | 50 | 53 | 54 |
| 75° C. % | 60 | 62 | 63 | 62 | 66 |
| DIN abrasion mm$^3$ | 95 | 120 | 129 | 138 | 158 |
| specific weight g/mm$^3$ | 1.12 | 1.12 | 1.12 | 1.12 | 1.12 |
| Compr. Set 24 h/70° C. % | 17 | 13 | 12 | 13 | 12 |

TABLE III

Comparison Example 2
Vulcanization of an SBR 1500 with sulfur/CBS
Sulfur/CBS = 2.2/1.2 phr

| Vulcanization system Properties | Vulcanization at 150° C. in 40 Min. | after 7 days aging at | | | |
|---|---|---|---|---|---|
| | | 100° C. | 110° C. | 120° C. | 130° C. |
| Tensile strength MPa | 22.0 | 18.3 | 9.5 | 6.2 | 3.6 |
| Elongation at break % | 427 | 309 | 124 | 35 | — |
| Modulus | | | | | |
| 100% MPa | 2.4 | 3.5 | 7.1 | — | — |
| 300% MPa | 13.1 | 17.7 | — | — | — |
| Tear resistance N/mm | 31 | 26 | 6.8 | — | — |
| Permanent set % | 8 | 5 | 2 | 1 | 1 |
| Hardness | | | | | |
| 22° C. Sh.A | 66 | 73 | 78 | 82 | 87 |
| 75° C. Sh.A | 60 | 69 | 75 | 78 | 85 |
| Elasticity | | | | | |
| 22° C. % | 44 | 60 | 57 | 41 | 38 |
| 75° C. % | 68 | 65 | 63 | 56 | 53 |
| DIN abrasion mm$^3$ | 108 | 118 | 159 | 167 | 220 |
| specific weight g/mm$^3$ | 1.12 | 1.12 | 1.12 | 1.12 | 1.12 |
| Compr. Set 24 h/70° C. % | 14 | 11 | 12 | 13 | 13 |

The preceding examples can be repeated with similar success by substituting the generically or specifically described reactants and/or operating conditions of this invention for those used in the preceding examples.

From the foregoing description, one skilled int he art can easily ascertain the essential characteristics of this invention, and without departing from the spirit and scope thereof, can make various changes and modifications of the invention to adapt it to various usages and conditions.

WHAT IS CLAIMED IS:

1. A process for vulcanizing rubber which comprises blending a sulfide derivative of an aromatic dithiocarboxylic acid of the formula (A—S—S—)$_z$ X —S—S—A' with an organic polymeric rubber to form a mixture and heating the mixture to a temperature in the range of 100° C. to 250° C. wherein A and A' are, independently, amine-free aromatic thiocarbonyl groups of formula I

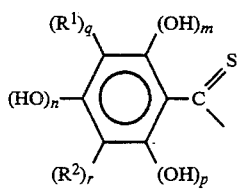

wherein n, m, p, q and r are 0 or 1 and the sum of n+m+p is at least 1,

R$^1$ and R$^2$ are, independently, C$_1$–C$_{10}$-alkyl radicals, alkenyl radicals with up to 10 carbon atoms (C$_1$–C$_{10}$) or aralykyl radicals with up to 15 carbon atoms, z is a natural number with 0<z<50, and x is a divalent or polyvalent (wherein z is greater than 1) linear or branched aliphatic, cycloaliphatic or araliphatic compound, or polymer having a degree of polymerization up to 50 and a valence of at least two, and where z=1, X is a C$_1$–C$_{30}$-alkylene radical, or alkyenylene radical with up to 30 carbon atoms (C$_1$–C$_{30}$), or aralkylene radical with up to 40 carbon atoms and wherein 1<4, X is a polyvalent C$_1$–C$_{20z}$ alkane, polyvalent alkene with up to 20z carbon atoms (C$_1$–C$_{20z}$) or polyvalent arylalkane with up to 20z carbon atoms.

2. A process as in claim 1, wherein the organic polymeric rubber is styrene-butadiene copolymer rubber, polybutadiene rubber, polyisoprene rubber, chloroprene rubber butyl rubber, ethylene-propylene, diene modified rubber, natural rubber, integral rubber or nitrile rubber.

3. A process according to claim 1, wherein said process comprises blending 1,2-bis-(4-hydroxy-3,5-ditertbutylbenzenethiocarbonyl dithio)ethane with said organic polymeric rubber.

4. A process according to claim 2, wherein said process comprises blending 1,2-bis-(4-hydroxy-3,5-ditertbutylbenzenethiocarbonyl dithio)ethane with said organic polymeric rubber.

* * * * *